United States Patent
Weber et al.

(10) Patent No.: US 8,664,434 B2
(45) Date of Patent: Mar. 4, 2014

(54) METHOD FOR PRODUCING ALIPHATIC CARBOXYLIC ACIDS FROM ALDEHYDES BY MICROREACTION TECHNOLOGY

(75) Inventors: Tonia Weber, Darmstadt (DE); Alexander Kaufmann, Dinslaken (DE); Oliver Borgmeier, Neuss (DE); Thorsten Kreickmann, Oberhausen (DE); Heinz Strutz, Moers (DE); Diana Utz, Fürth (DE); Elias Klemm, Nürnberg (DE); Claudia Liebold, Chemnitz (DE)

(73) Assignee: Oxea GmbH, Oberhausen (DE)

( * ) Notice: Subject to any disclaimer, the term of this patent is extended or adjusted under 35 U.S.C. 154(b) by 272 days.

(21) Appl. No.: 13/138,719

(22) PCT Filed: Mar. 3, 2010

(86) PCT No.: PCT/EP2010/001298
§ 371 (c)(1),
(2), (4) Date: Oct. 21, 2011

(87) PCT Pub. No.: WO2010/108586
PCT Pub. Date: Sep. 30, 2010

(65) Prior Publication Data
US 2012/0035393 A1    Feb. 9, 2012

(30) Foreign Application Priority Data
Mar. 24, 2009 (DE) .......................... 10 2009 014 626

(51) Int. Cl.
*C07C 51/16* (2006.01)

(52) U.S. Cl.
USPC ....................................... 562/531

(58) Field of Classification Search
None
See application file for complete search history.

(56) References Cited

U.S. PATENT DOCUMENTS 8,492,584 B2 *  7/2013  Teles et al. ............... 562/533

FOREIGN PATENT DOCUMENTS

| DE | 100 10 770 | 9/2001 | ............ C07C 51/235 |
| GB | 931589 | 7/1963 | |
| WO | 2004/108648 | 12/2004 | ............ C07C 51/00 |
| WO | 2009/024549 | 2/2009 | ............ C07C 51/235 |

OTHER PUBLICATIONS

Efrenfeld W et al: "Microreactors: New Technology for Modern Chemistry", Jan. 1, 2000, pp. 1-14, XP002465177, ISBN: 978-3-527-29590-6.*
International Search Report Efrenfeld W et al: "Microreactors: New Technology for Modern Chemistry" Jan. 1, 2000, pp. 1-14, XP002465177 ISBN: 978-3-527-29590-6 Abschnitte 1.2, 1.3.
Unbekannter Autor: "Gezähmte Chemie im Mikroreaktor" VDI Nachrichten, Jun. 2, 2000, XP002597026 Gefunden im Internet: URL:http://www.vdi-nachrichten.com/vdi-nachrichten/aktuelle_ausgabe/akt_ausg_detail.asp?cat=2&id=2895&doPrint=1> [gefunden am Aug. 18, 2010].

* cited by examiner

*Primary Examiner* — Karl J Puttlitz
(74) *Attorney, Agent, or Firm* — Michael W. Ferrell

(57) ABSTRACT

A process for preparing aliphatic carboxylic acids having 3 to 10 carbon atoms by oxidizing the corresponding aldehydes with oxygen or oxygen-containing gases, characterized in that (i) the oxidation is performed in a microreactor at elevated pressure and with an oxygen excess based on the stoichiometrically required amount of oxygen, and (ii) in that the reaction mixture removed from the microreactor is passed through at least one postreactor without further addition of oxygen, and (iii) wherein the oxidation reaction in the microreactor is performed under such conditions that aldehyde and corresponding peracid formed are present in the reaction mixture removed in a molar ratio within a range of 1:(0.9 to 1.1), preferably of 1:(0.95 to 1.05).

17 Claims, 2 Drawing Sheets

METHOD FOR PRODUCING ALIPHATIC CARBOXYLIC ACIDS FROM ALDEHYDES BY MICROREACTION TECHNOLOGY

CROSS-REFERENCE TO RELATED APPLICATIONS

This application is based on International Patent Application No. PCT/EP2010/001298 (International Application Publication No. WO 2010/108586) filed Mar. 3, 2010, which is based on German Patent Application No. DE 10 2009 014 626.1, filed Mar. 24, 2009. The priorities of the foregoing applications are hereby claimed and their disclosures incorporated herein by reference in their entireties.

TECHNICAL FIELD

The present invention relates to a process for preparing aliphatic carboxylic acids from aldehydes by oxidation with oxygen or oxygen-containing gases by microscale reaction technology at elevated pressure and with an oxygen excess.

BACKGROUND

Aldehydes are the usual starting materials for obtaining carboxylic acids. Their preferential position for this field of use is due to their varied availability and the oxidative conversion of the carbonyl group to the carboxyl group. In the context of processes practiced industrially, aldehydes are converted to carboxylic acids predominantly in the presence of catalysts. However, there are also known processes in which the use of catalysts is dispensed with. To avoid side reactions, minimum temperatures are employed both in the catalytic and in the noncatalytic processes; in general, a reaction temperature of 100° C. is not exceeded. Useful catalysts include predominantly salts of transition metals, especially salts of cobalt and of manganese, and of chromium, iron, copper, nickel, silver and vanadium. Frequently, carboxylic acid formation from aldehydes, even when observing optimal temperature conditions, is associated with side reactions and degradation reactions. This is equally true for reactions in the presence and in the absence of catalysts. In such cases, the selectivity of the conversion can be improved considerably by addition of alkali metal salts of weak acids to the reactants. However, a disadvantage in this process variant is that the salts have inhibiting action, and so the reaction time has to be prolonged for a full conversion of the starting materials. The oxidation of aliphatic aldehydes to the corresponding carboxylic acids using oxygen is a process which has been operated on the industrial scale for many years. Important aliphatic carboxylic acids which are placed by this process are the isomeric butyric acids, the isomeric pentanoic acids, 2-ethylhexanoic acid, n-heptanoic acid, n-nonanoic acid, and isononanoic acid based on 3,5,5-trimethylhexanoic acid (Ullmann's Encyclopedia of Industrial Chemistry, Wiley-VCH, 6$^{th}$ edition, volume 6, chapter "Carboxylic Acids, Aliphatic"; K. Weissermel, H.-J. Arpe, Industrielle Organische Chemie [Industrial organic chemistry], VCH Verlagsgesellschaft, 3rd edition, 1988, chapter "Oxo-Carbonsauren" [Oxo carboxylic acids]).

In a conventional embodiment of the oxidation of aliphatic aldehydes, the aldehyde is initially charged in a suitable reactor, for example in a tubular reactor provided with a baffle plate and optionally also containing random packing, and the oxygen or the oxygen-containing gas mixture is passed through the aldehyde from the bottom. Such a procedure using a bubble column is described, for example, in DE 100 107 69 C1, DE 100 107 70 C1 and DE 100 107 71 C1. The reaction of the liquid aliphatic aldehyde with gaseous oxygen is performed generally at temperatures of preferably 40 to 80° C. and at standard pressure. Higher reaction temperatures and pressures are possible, but the reaction temperature selected should not exceed 100° C. and the pressure should not be higher than 1 MPa. Both noncatalytic processes (DE 100 107 69 C1, DE 100 107 69 C1) and transition metal-catalyzed processes (DE 100 107 71 C1; G. R. Lappin, J. G. Sauer "Alpha Olefins Applications Handbook", Marcel Dekker Inc., New York and Basel, 1989, Chapter 11, "Fatty Acids") are known.

In a further embodiment, the reactor used is a trickle tower containing shaped bodies. The aldehyde is allowed to trickle downward through the packing, and oxygen or an oxygen-containing gas mixture is introduced simultaneously into the tower in cocurrent or counter-current. In addition, the prior art also describes the use of stirred tanks in aldehyde oxidation with gaseous oxygen (WO2001/46111 A1).

The industrial oxidation of aliphatic aldehydes with gaseous oxygen in high-capacity conventional reactors is constantly being optimized and is now being implemented at high conversion with good carboxylic acid selectivities. Disadvantages, however, are the comparatively long residence times of the reaction mixture, which may be up to several hours and impair the economic viability of the oxidation process. In the case of long residence times in the oxidation reactors, increased by-product formation is additionally to be expected, for example with cleavage products such as lower carboxylic acids, carbon monoxide or carbon dioxide, and so the selectivity of the oxidation reaction can suffer in spite of the good values which have now been achieved. The handling of aliphatic aldehydes and oxygen in high-capacity reactors likewise entails a high level of capital costs and control complexity for safety devices. Due to the exothermic oxidation reaction, it also has to be ensured that the heat of reaction released can be removed in a rapid and controlled manner in order to avoid an unwanted temperature rise. Therefore, cooling devices of appropriate dimensions should be installed. For lowering of the residence time, working at elevated pressures can be contemplated, but the employment thereof in the oxygen oxidation of aliphatic aldehydes in high-capacity reactors can become very problematic for safety reasons and entails high capital costs. Aldehyde oxidations implemented industrially are therefore usually conducted at standard pressure or if appropriate only slightly elevated pressure.

The constant advance in miniaturization in information and communications technology since the 1960s has also found its way into the field of chemistry since the 1980s, first in the laboratory and in the last few years also increasingly in production. While the miniaturization of reaction spaces is utilized in high-throughput studies to test a particular reaction in a small space in a parallel manner under a maximum number of different conditions in order, for example, to develop suitable catalysts in a controlled manner (WO 00/51720), miniaturization in microscale reaction technology serves for performance of a chemical reaction under the same conditions in a multitude of parallel reaction spaces in order to be able to prepare corresponding amounts of chemical products under defined conditions. The transition from the macroscopic process regime to microscale reaction technology offers the following advantages in terms of process technology: As a result of the small lateral dimensions, heat and mass transfer operations by thermal conduction and diffusion are greatly intensified and enable high performances for heat exchangers and mixers. In exothermic reactions, the heat of reaction can therefore be removed much more rapidly than in high-capacity conventional reactors. A characteristic feature of microscale reaction technology is the high ratio of surface to volume, i.e. the high specific surface area, such that surface-controlled phenomena too can also be distinctly intensified.

As a result of these intensifications, higher space-time yields, i.e. shorter residence times, are possible. The intensification potential of the micro-reactors is fully exploited especially when new reaction conditions which are unusual for conventional reactors or cannot be realized in such conventional reactors are established. Reference is made in this context to "novel process windows", a term known, for example, from Energy Environ. Sci., 2008, 1, pages 467-478. Especially the establishment of higher pressures and temperatures is possible as a result. An additional factor is the safety aspect that these conditions frequently cannot be controlled in high-capacity conventional reactors and can be established safely only in microreactors. However, even without this intensification potential, i.e. without the use of unusually high pressures and temperatures, the micro-reactor can enable safer operation than with conventional technology.

Typical apparatus dimensions for microscale reaction technology are within a range from a few millimeters to a few micrometers. For the manufacture of microscale process technology components in these dimensions, suitable structuring methods are available, for example precision engineering processes such as microscale machining or microscale spark erosion, laser ablation processes, forming and molding processes or etching processes. In the case of dimensions below 100 nanometers in particular, reference is made to nanotechnology, whereas apparatus dimensions above a few millimeters pertain basically to milliscale apparatus. These are then followed by conventional reactors such as shell-and-tube apparatus, tubular reactors and finally stirred tanks.

An overview of the field of microscale process technology and of the manufacture of microscale process technology components can be found in Winnacker, Küchler, Chemische Technik [Chemical Technology], Wiley-VCH, 5$^{th}$ edition, 2004, volume 2, chapter 8 "Mikroverfahrenstechnik" [Microscale Process Technology], and in Microreactors in Organic Synthesis and Catalysis, Wiley-VCH, 2008, chapter 1 "Fabrication of Microreactors Made from Metals and Ceramics" and chapter 2 "Fabrication and Assembling of Microreactors Made from Glass and Silicon".

Against the background of the above-outlined disadvantages possessed by the oxidation of aliphatic aldehydes with oxygen or oxygen-containing gases in conventional high-capacity reactors, it is an object of the present invention to provide a process for oxidation of aliphatic aldehydes to the corresponding carboxylic acids which, at high aldehyde conversion and high selectivities for the desired carboxylic acids, enables a lowering of the residence time. The associated increase in the space-time yield of the desired carboxylic acid increases the economic viability of the oxidation process. The process to be provided shall also be operated in a safer manner and feature lower capital costs for safety devices.

SUMMARY OF THE INVENTION

The present invention therefore relates to a process for preparing aliphatic carboxylic acids having 3 to 10 carbon atoms by oxidizing the corresponding aldehydes with oxygen or oxygen-containing gases. It is characterized in that the reaction is performed in a microreactor at elevated pressure and with an oxygen excess based on the stoichiometrically required amount of oxygen, and in that the reaction mixture removed from the microreactor is passed through at least one postreactor without further addition of oxygen, and wherein the oxidation reaction in the microreactor is performed under such conditions that aldehyde and corresponding percarboxylic acid formed are present in the reaction mixture removed in a molar ratio within a range of 1:(0.9 to 1.1), preferably of 1:(0.95 to 1.05).

BRIEF DESCRIPTION OF THE DRAWINGS

The invention is described in detail below with reference to the drawings, wherein.

DETAILED DESCRIPTION

Figure 1:
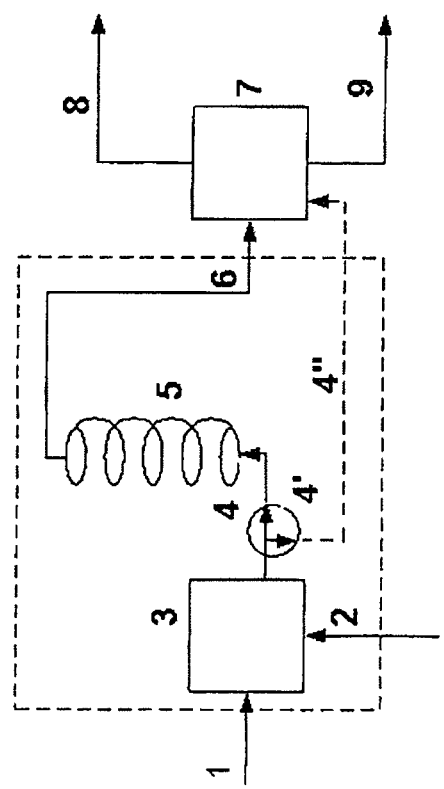
FIG. 1 is a schematic diagram showing a microreactor apparatus suitable for use in connection with the present invention.

In the oxidation process performed in accordance with the invention by means of microscale reaction technology, gaseous oxygen or an oxygen-containing gas is contacted with the liquid aliphatic aldehyde. Therefore, in the microreactor, for example in a microscale capillary reactor with microchannels, gas/liquid multiphase flows will form, which, according to the flow rate of the gaseous and liquid phases, exhibit particular flow characteristics. A distinction is made here between a bubble flow in which the gas phase is in disperse form and the gas bubbles are virtually spherical and the diameters thereof are less than the diameter of the microchannel, a plug flow in which the gas phase is still in disperse form but the gas bubbles have a cylindrical shape of different length and fill the entire cross section of the microchannel, which results in segmentation into alternating gas and liquid plugs, and a ring flow in which the gas phase forms a continuous core flow with a liquid film at the microchannel wall. The flow characteristics of gas-liquid multiphase flows are discussed in Winnacker, Kuchler, Chemische Technik, Wiley-VCH, 5$^{th}$ edition, 2004, volume 2, chapter 3 "Mikrofluidik" [Microfluidics].

For aldehyde oxidation with oxygen or oxygen-containing gases by the process according to the invention, suitable microreactors are all of those in which a heterogeneous gas/liquid flow forms in the reaction of the gaseous oxygen-containing phase with the liquid aldehyde-containing phase. The flow characteristics of bubble, plug or ring flow which develop, or mixtures thereof, ensure sufficient mixing of the gaseous with the liquid phase. Examples of microreactors suitable for the performance of the process according to the invention are known from Chemical Micro Process Engineering, Wiley-VCH, 2004, chapter 5.1 "Micro Reactors for Gas/Liquid Reactions". Particularly suitable microreactors are microscale capillary reactors or microscale bubble column reactors with microchannels of appropriate dimensions, in which the aforementioned flow characteristics can develop. Such microreactors are described, for example, in Microreactors in Organic Synthesis and Catalysis, Wiley-VCH, 2008, chapter 4.4 "Gas-Liquid Reactions" or in Fortschritts-Berichte VDI, series 3 No. 771, VDI Verlag GmbH, Dusseldorf 2003. It is likewise possible to arrange a multitude of microreactors with microchannels of appropriate dimensions in parallel in a multichannel system.

It is additionally possible to operate a micromixer upstream of the actual microreactor, for example upstream of the microscale capillary reactor, and then to supply the reaction mixture to the microreactor. Suitable mixer types are known, for example, from Winnacker, Kuchler, Chemische Technik, Wiley-VCH, 5$^{th}$ edition, 2004, volume 2, chapter 4.2 "Mischen" [Mixing] or in Chemical Micro Process Engineering, Wiley-VCH, 2004, chapter 4.1 "Micro Reactors for Liquid-phase and Liquid/Liquid-phase Reactions". These mixer types which were designed initially for the intensive mixing of liquids are likewise suitable for the mixing of a gaseous phase with the liquid phase.

In such micromixers, the liquid phase and the gaseous phase are introduced into the mixer via capillary feed lines, mixed in a mixing chamber and removed from the mixing chamber. It is also possible that the two capillary feed lines open in a region which is the starting point of a capillary removal line in which the heterogeneous gas/liquid mixture is supplied to the microreactor. When the capillary feed lines are arranged at an angle of about 180° and thus the gaseous and liquid phases meet one another in a frontal manner and the capillary removal line is arranged at an angle of about 90° to the opening region of the capillary feed lines, the result is a T-shaped mixing device. In addition, the two capillary feed lines may also be arranged at an angle between 90 and 180° or at an angle between 0 and 90°, and together with the capillary removal line form a Y-shaped mixing device.

Particularly suitable reactors have been found to be microscale capillary reactors. Microscale capillary reactors may be a single microcapillary which is preferably preceded upstream by a micromixer. Additionally suitable are also those microscale capillary reactors in which a plate is provided with microscale grooves which form a multitude of parallel microscale reaction channels. Such an arrangement of parallel microscale reaction channels can also be operated as a microscale bubble column reactor in which the liquid phase is supplied to the top region of the plate arranged vertically and the liquid film falls in the direction of the base. The gaseous phase can be supplied in cocurrent, countercurrent or crosscurrent. DE 102 57 239 B3 discloses a suitable microscale bubble column reactor in which a liquid olefin-containing solution is oxidized with gaseous oxygen in the presence of a photosensitizer in a heterogeneous reaction system.

WO 2007/027785 A2 describes the reaction of a hydrogen-containing organic compound, for example of a hydroquinone derivative, with gaseous oxygen in a micro-reactor to form the hydrogen peroxide target product. The microreactor used may, for example, be a parallel arrangement of a multitude of microscale reaction channels.

DE 10 2004 049 730 A1 discloses the catalytic oxidation of organic compounds using a microscale capillary reactor comprising at least two static mixers, wherein two liquids not homogeneously miscible with one another are combined in the first mixer and the liquid heterogeneous phase thus obtained is passed into a downstream second mixer in which a gaseous component is introduced via a separate capillary line. The resulting liquid/liquid/gaseous mixture is subsequently passed through a capillary. One liquid phase is an organic phase comprising at least one organic, oxygen-oxidizable reactant dissolved therein, and the other liquid phase is an aqueous solution comprising the dissolved oxidation catalyst. Oxygen is passed into the second mixer as a gaseous phase.

The oxidation of n-butyraldehyde by means of gaseous oxygen in a microscale bubble column is discussed in Microreaction Technology, IMRET: Proceedings of the 5$^{th}$ International Conference on Microreaction Technology; Springer-Verlag, 2001, pages 202-214 and in Fortschritts-Berichte VDI series 3 No. 771, VDI Verlag GmbH, Dusseldorf 2003; pages 108-125 and 143-144. The conversion characteristics in the microscale bubble column are influenced to a crucial degree by the interaction between the specific surface area and the residence time, and the comparison of the experimentally found conversion data with a model calculation conducted for the microscale bubble column can be used to calculate, for a given liquid volume flow, an optimal n-butyraldehyde conversion for a particular specific surface area and residence time. The reported conversion figures are in the region of 40%, based on aldehyde used.

It has been found to be useful to oxidize the aldehydes in the novel process at temperatures between 0 and 130° C., preferably between 20 and 100° C. and especially between 40 and 80° C. The conversion is undertaken at a constant temperature, or a virtually constant temperature within the technical means. To maintain a constant temperature, the microreactor can be disposed in a vessel containing a heat carrier medium. Pumped circulation of the heat carrier medium continuously removes or supplies heat. In addition, microscale heat exchanger plates can likewise be mounted in the microreactors, through which the heat carrier medium flows and ensures a constant temperature in the micro-reactor.

The reaction mixture removed from the microreactor is first expanded to standard pressure in a pressure separator, wherein a liquid phase separates out to form offgas. The oxygenous offgas is discharged and the liquid phase is removed for further workup.

In the process according to the invention, the liquid reaction product obtained in the pressure separator from the first reaction stage is supplied to a second reaction stage which is likewise effected in a microreactor. The microreactor used in the second reaction stage may be identical in design to the microreactor used in the first stage, but it may also be a customary microreactor of different design.

The separated liquid phase from the first reaction stage is pumped after the expansion step without further addition of oxygen into the second microreactor, wherein a liquid pressure develops as a result of the pumping operation. The first microreactor can therefore be interpreted as the oxidation reactor, and the second microreactor as a postreactor. Since no gaseous phase is fed to the second microreactor, it is also possible for this process step to use microreactors which need not necessarily ensure good mass transfer between a gaseous and liquid phase. The second microreactor or postreactor is adjusted by suitable heat exchanger units to a temperature corresponding to the temperature in the first microreactor. It is also possible to operate the postreactor at a lower temperature, in which case the temperature difference is 5 to 50° C., preferably 10 to 20° C. In this two-stage mode of operation, preference is given to operating microreactor and postreactor at the same temperature.

Optionally, the reaction mixture obtained downstream of the second microreactor can be pumped once again through a third or through further microreactors without addition of oxygen. In this embodiment of the process according to the invention, the conversion in the first microreactor is thus effected at elevated pressure and with an oxygen excess based on the amount of oxygen required stoichiometrically, while the reaction is ended after the expansion step in a cascade of downstream microreactors or postreactors without active addition of oxygen. The microreactors in the postreaction cascade can be operated at the temperature of the first microreactor. It is likewise possible to establish a temperature difference between adjacent stages within the postreactor cascade, in which case the temperature decreases from stage to stage. The temperature difference may be between 5 and 50° C., preferably 10 to 20° C. The temperature figures specified are merely guide values which should be matched in the individual case to the specific circumstances. If more than two reaction stages are employed, i.e. the conversion under oxygen pressure in the first microreactor and a postreaction stage, it is not necessary to maintain equal temperature differences between the individual stages. The temperature differences can instead be selected variably and be aligned to the individual requirements. The crude acid mixture which flows out of the second microreactor, or out of the last microreactor in the case of a plurality of postreactors, is collected in a receiver and can then be distilled by known distillation processes to give the pure material.

Surprisingly, in the two-stage or multistage process regime, the carboxylic acid selectivity can be improved once again compared to the one-stage mode of operation when the oxidation reaction in the first microreactor is performed at elevated pressure and with an oxygen excess based on the stoichiometrically required amount, under such conditions that aldehyde and percarboxylic acid formed are present in the reaction output in a molar ratio within a range of 1:(0.9 to 1.1), preferably of 1:(0.95 to 1.05). Without entering into exact mechanistic considerations, it can be assumed that the aldehyde conversion in the first reaction stage under these reaction conditions is still incomplete, and percarboxylic acid and aldehyde are present in approximately the same molar ratio in the reaction output, and then are depleted by a controlled reaction in the postreactor by a Baeyer-Villiger reaction to give the desired carboxylic acid. The two-stage or multistage mode of operation can effectively suppress the uncontrolled decomposition of the percarboxylic acid which impairs the selectivity of the conversion. In this type of reaction regime, the aim in the first reaction stage performed at elevated pressure and with oxygen excess is thus merely a partial conversion of aldehyde. The residual amounts of aldehyde are then consumed in the postreaction by the reaction with the percarboxylic acid. In the two-stage or multistage mode of operation, the oxidation reaction is preferably performed at a pressure of 0.4 to 2.0 MPa and with an oxygen excess corresponding to up to twice the amount of oxygen required, and the resulting reaction mixture is passed without further active addition of oxygen through a second or several downstream postreactors likewise designed as microreactors.

The use of microreactors not only in the first oxidation reaction conducted with addition of oxygen but also in the downstream postreaction stage allows the residence time likewise to be reduced significantly compared to an aldehyde oxidation process performed conventionally in high-capacity reactors. Thus, the residence time per reactor stage is 0.5 to 10 minutes, preferably 1 to 5 minutes. At the same time, excellent aldehyde conversions and carboxylic acid selectivities are observed in the crude acid mixture leaving the last postreactor.

Irrespective of whether the oxidation reaction is conducted in one microreactor or in combination with one or more postreactors, at least one postreactor being designed as a microreactor, the microreactors used generally have a reaction space with a diameter of 1 millimeter to 0.01 millimeter.

At the center of the novel process is the oxidation of unbranched and branched $C_3$ to $C_{10}$ aldehydes. The origin of the aldehydes is not restricted to particular preparation processes. Due to their ease of obtainability, aldehydes obtained by the oxo process, i.e. by reaction of $C_2$ to $C_9$ olefins with carbon monoxide and hydrogen, are preferred. In this context, it is not crucial which specific embodiment of the oxo process served to provide the aldehydes, i.e. whether the reaction was catalyzed, for example, by cobalt or by rhodium, whether the metals were used alone or together with complexing agents and whether the catalyst was homogeneously dissolved in the reaction mixture or formed a separate heterogeneous phase.

The process according to the invention is particularly suitable for preparation of propionic acid, n-butyric acid, isobutyric acid, n-pentanoic acid, 2-methyl-butyric acid, 3-methylbutyric acid, n-hexanoic acid, 2-methylpentanoic acid, n-heptanoic acid, 2-methyl-hexanoic acid, 2-ethylhexanoic acid, 2-propylheptanoic acid, n-nonanoic acid, 2-methyloctanoic acid and iso-nonanoic acid with the main constituent 3,5,5-tri-methylhexanoic acid, the corresponding aldehyde being obtainable by the oxo process from diisobutylene.

The oxidizing agent used in the process of the invention is molecular oxygen or gas mixtures comprising molecular oxygen. Further constituents of such gas mixtures are inert gases, for example nitrogen, noble gases and carbon dioxide. The proportion of the inert constituents of the oxygen-containing gas mixture is up to 90% by volume, especially 30 to 80% by volume. The preferred oxidizing agents are oxygen or air.

The aldehydes can be used as such or dissolved in a solvent which is inert under the reaction conditions. Examples of suitable solvents are ketones such as acetone, esters, for example ethyl acetate, hydro-carbons, for example toluene, and nitrohydrocarbons such as nitrobenzene. The concentration of the aldehyde is limited by the solubility thereof in the solvent.

The process according to the invention is generally performed continuously. Recycling of unconverted reaction participants is possible.

In order to increase the amount of reaction product from the aldehyde oxidation per unit time, parallel operation of a multitude of microchannels in a multi-channel system, and of microreactors, for example microscale bubble columns, is possible. In this way, the amount produced is increased and the advantages of microscale reaction technology, such as high specific surface area and good heat removal, can be utilized at the same time.

The examples which follow describe the preparation of n-pentanoic acid and isononanoic acid by the process claimed.

It will be appreciated that the novel process is not restricted to the embodiments described below.

EXAMPLES

Figure 2:
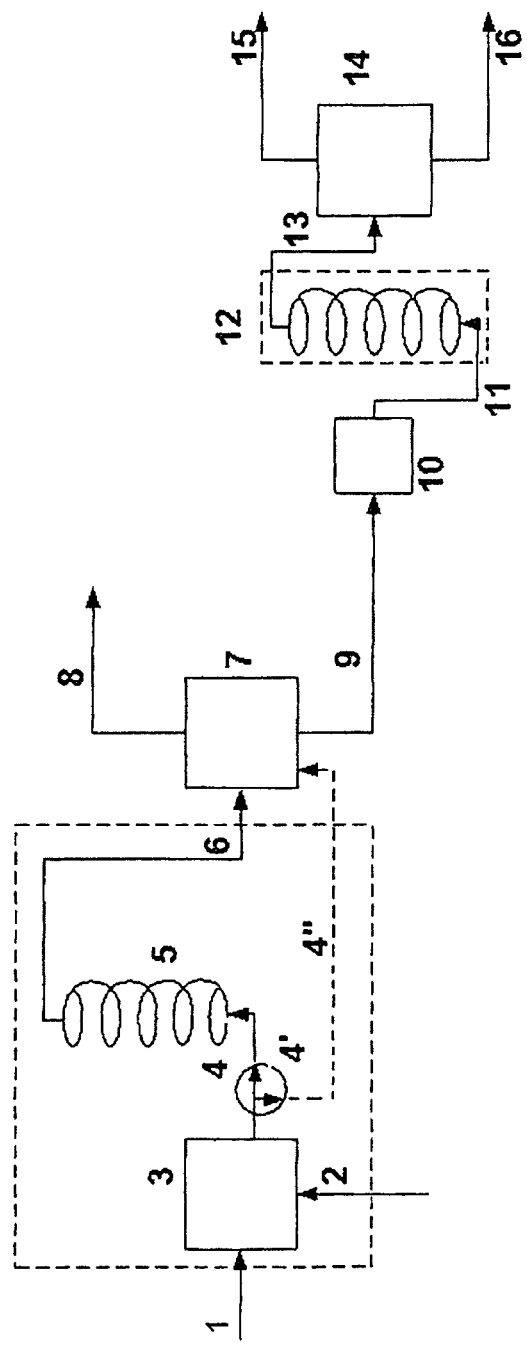
FIG. 2 is a schematic diagram showing a two-step reactor system suitable for use in connection with the present invention.

The liquid phase oxidation of the aldehydes used is performed according to the test setup which follows, and which is shown in principle in FIGS. 1 and 2. Liquid aldehyde is supplied via line (1), and gaseous oxygen via line (2), to the micromixer (3), which is a microscale T-piece with an internal diameter of 0.75 mm. The reactant mixture is subsequently supplied via line (4), which likewise has an internal diameter of 0.75 mm, to a three-way tap (4'). For the analysis of the reactant stream, the three-way tap (4') is set in a kind of bypass mode, in which the reactant stream bypasses the microreactor (5) via line (4") and flows directly into a pressure separator (7) in which it is expanded. The liquid phase obtained is analyzed by gas chromatography. In working operation, the three-way tap (4') is adjusted such that the reactant stream flows into the microreactor (5). The microreactor (5) consists of a microcapillary of length 5 m with an internal diameter of 0.75 mm. The reactant mixture enters the microreactor (5) from the bottom and the product mixture is removed at the top thereof via line (6) and supplied to the pressure separator (7) in which the product mixture is expanded to standard pressure. Oxygenous offgas is discharged via line (8), while the crude acid obtained is withdrawn via line (9) and purified by distillation by conventional processes. The microreactor (5) and the micromixer (3) are in a temperature control cell which is indicated schematically. The temperature control cell is heated by means of a thermostat.

FIG. 2 describes, in schematic terms, the two-stage reaction regime. Reference numerals (1)-(9) are as defined above. The liquid crude mixture conducted out of the pressure separator (7) of the first reaction stage via line (9) is supplied by means of the piston pump (10) via line (11) with an internal diameter of 0.75 mm to the second microreactor (12) or postreactor from the bottom. The microreactor (12) is likewise a microcapillary with a length of 5 m at an internal diameter of 0.75 mm. The crude product is removed at the top of the second microreactor and conducted via line (13) into a receiver (14). Gaseous components are withdrawn via line (15), and the crude acid is introduced into the distillative workup via line (16). The second microreactor is likewise within a temperature control device which is indicated schematically.

The particular aldehyde is supplied to the micromixer (3) via line (1) in an amount of 0.9 ml/min by means of a piston pump, and oxygen from a gas bottle via line (2) in an amount of 140 ml/min. The molar ratio of oxygen to aldehyde is 1.5; the residence time of the aldehyde in the first microreactor in which the reaction with oxygen is effected, and in the second microreactor or postreactor, is in each case 2.5 min.

Aldehyde conversion and selectivity of the aldehyde converted to carboxylic acid is determined by gas chromatography analyses of the reactant mixture bypassing the microreactor, and by the gas chromatography analysis of the crude acids obtained via line (9) (one-stage mode) or via line (16) (two-stage mode) in working operation. The aldehyde conversion is then calculated from the amounts of aldehyde determined from the gas chromatograms recorded in bypass and working operation.

The carboxylic acid selectivity is calculated from the amounts of carboxylic acid determined by gas chromatography in working operation minus bypass operation (caused by acid traces already present in the starting aldehyde), based on the amounts of aldehydes determined by gas chromatography in working operation and in bypass operation.

Preparation of N-Pentanoic Acid

1. One-Stage Mode (Comparative Example)

The liquid phase oxidation of n-pentanal to n-pentanoic acid is effected according to the process scheme in FIG. 1 at a constant reaction temperature of 80° C. under the conditions specified in the general description. Table 1 below reports the n-pentanal conversions and the selectivities for n-pentanoic acid as a function of the oxygen pressure set.

TABLE 1 n-Pentanal conversions and selectivities for n-pentanoic acid as a function of oxygen pressure at 80° C.

| Experiment No. | Pressure [MPa gauge] | n-Pentanal conversion (%) | Selectivity (%) for n-pentanoic acid |
|---|---|---|---|
| 1 | 0.4 | 82 | 91 |
| 2 | 1.5 | 89 | 85 |
| 3 | 2.0 | 98 | 80 |

With rising oxygen pressure, the n-pentanal conversion increases significantly, but the n-pentanoic acid selectivity falls at the same time due to the increased formation of peracid, which subsequently decomposes in an uncontrolled manner with loss of selectivity. Nevertheless, compared to known aldehyde oxidation reactions performed by means of microreactors, much higher yield values of n-pentanoic acid are observed.

2. Two-Stage Mode

The liquid phase oxidation of n-pentanal to n-pentanoic acid is effected according to the process scheme in FIG. 2 at a constant reaction temperature of 80° C. in the first microreactor, at a constant liquid pressure of 3.4 MPa in the second microreactor (postreactor) and under the conditions specified in the general description. Table 2 below reports the n-pentanal conversions and the selectivities for n-pentanoic acid as a function of the oxygen pressure set and as a function of the temperature in the second microreactor (postreactor).

TABLE 2 n-Pentanal conversions and selectivities for n-pentanoic acid as a function of oxygen pressure and of temperature in the second microreactor; constant temperature in the first microreactor at 80° C. and constant liquid pressure of 3.4 MPa in the second microreactor

| Experiment No. | Pressure [MPa gauge] 1st microreactor | Temperature (° C.) 2nd microreactor | n-Pentanal conversion (%) | Selectivity (%) for n-pentanoic acid |
|---|---|---|---|---|
| 4 | 0.4 | 30 | 82 | 91 |
| 5 | 0.4 | 70 | 80 | 99 |
| 6 | 0.4 | 80 | 79 | 95 |
| 7 | 1.5 | 80 | 98 | 92 |
| 8 | 2.0 | 80 | Total oxidation | |

In experiments 4 and 5, a selectivity increase for n-pentanoic acid is observed in the case of a temperature increase in the second microreactor, and so a controlled depletion by reaction of the peracid can be assumed. Experiment 7 exhibits improved conversion and selectivity values compared to the one-stage mode according to experiment 2. It can be assumed here that per-n-pentanoic acid and the remainder of n-pentanal are present in a molar ratio of about 1:1 in the discharge from the first microreactor, and so there is further n-pentanoic acid formation with consumption of n-pentanal via a Baeyer-Villiger oxidation in the second microreactor (postreactor).

In experiment 8, the conversion in the first microreactor is at first performed according to the reaction conditions in example 3. In the subsequent postreaction at the same temperature, satisfactory results are no longer observed. In this reaction configuration, it can be assumed that barely any n-pentanal is still present in the reaction output of the first reaction stage and, in addition to n-pentanoic acid, a comparatively high concentration of per-n-pentanoic acid is present, which decomposes in an uncontrolled manner in the postreaction stage.

Preparation of Isononanoic Acid (Comparative Example)

The liquid phase oxidation of isononanal to isononanoic acid is effected according to the process scheme in FIG. 1 at a constant reaction temperature of 80° C. under the conditions specified in the general description. Table 3 below reports the isononanal conversions and the selectivities for isononanoic acid, based in each case on the main isomer 3,5,5-trimethylhexanal or 3,5,5-trimethylhexanoic acid as a function of the oxygen pressure established.

TABLE 3

Isononanal conversions and selectivities for isononanoic acid as a function of oxygen pressure at 80° C.

| Experiment No. | Pressure [MPa] | Isononanal conversion (%) | Selectivity (%) for isononanoic acid |
|---|---|---|---|
| 9 | 0.4 | 64 | 88 |
| 10 | 0.6 | 84 | 86 |
| 11 | 0.8 | 90 | 86 |

With rising oxygen pressure, the isononanal conversion rises significantly, but the isononanoic acid selectivity falls at the same time due to the increased formation of peracid, which subsequently decomposes in an uncontrolled manner with loss of selectivity. Nevertheless, in the isononanal oxidation too, much higher yields of the desired carboxylic acid are observed compared to known aldehyde oxidation reactions performed by means of microreactors.

While the invention has been described in detail, modifications within the spirit and scope of the invention will be readily apparent to those of skill in the art. In view of the foregoing discussion, relevant knowledge in the art and references including co-pending applications discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

The invention claimed is:

1. A process for preparing aliphatic carboxylic acids having 3 to 10 carbon atoms by oxidizing the corresponding aldehydes with oxygen or oxygen-containing gases, characterized in that the oxidation is performed in a microreactor having a reaction space with a diameter of 1 millimeter to 0.01 millimeter at elevated pressure and with an oxygen excess based on the stoichiometrically required amount of oxygen, and in that the reaction mixture removed from the microreactor is passed through at least one postreactor without further addition of oxygen, wherein said aliphatic carboxylic acid is prepared in said postreactor and wherein the oxidation reaction in the microreactor is performed under such conditions that aldehyde and corresponding peracid formed are present in the reaction mixture removed from the microreactor in a molar ratio within a range of 1:(0.9 to 1.1).

2. The process as claimed in claim 1, characterized in that aldehyde and corresponding peracid formed are present in the reaction mixture removed from the microreactor in a molar ratio within a range of 1:(0.95 to 1.05).

3. The process as claimed in claim 1, characterized in that the oxidation is effected at a temperature of 0° C. to 130° C.

4. The process as claimed in claim 3, characterized in that the oxidation is effected at a temperature of 20° C. to 100° C.

5. The process as claimed in claim 3, characterized in that the oxidation is effected at a temperature of 40° C. to 80° C.

6. The process as claimed in claim 1, characterized in that the microreactor and the postreactor directly downstream are operated at the same temperature.

7. The process as claimed in claim 1, characterized in that the microreactor and at least one postreactor are operated at different temperatures, the temperature decreasing from stage to stage and the temperature difference between adjacent stages being 5° C. to 50° C.

8. The process as claimed in claim 7, characterized in that the microreactor and at least one postreactor are operated at different temperatures, the temperature decreasing from stage to stage and the temperature difference between adjacent stages being 10° C. to 20° C.

9. The process as claimed in claim 1, characterized in that the oxidation reaction is performed at a pressure of 0.4 to 2.0 MPa and with up to twice the stoichiometrically required amount of oxygen.

10. The process as claimed in claim 1, characterized in that the oxidizing agent is molecular oxygen.

11. The process as claimed in claim 1, characterized in that the oxidizing agent is a gas mixture comprising molecular oxygen and up to 90% by volume of inert gases.

12. The process as claimed in claim 1, characterized in that the oxidizing agent is a gas mixture comprising molecular oxygen and of from 30 to 80% by volume of inert gases.

13. The process as claimed in claim 12, characterized in that the gas mixture is air.

14. The process as claimed in claim 1, characterized in that the aliphatic carboxylic acid is n-butyric acid, n-pentanoic acid, 2-methylbutyric acid, 2-ethylhexanoic acid, 2-propylheptanoic acid or isononanoic acid.

15. The process as claimed in claim 1, characterized in that the microreactor is a microcapillary or a microscale bubble column reactor.

16. The process as claimed claim 1, characterized in that several microreactors arranged in parallel are operated.

17. The process as claimed in claim 1, characterized in that at least one postreactor is a microreactor.

* * * * *